United States Patent [19]

Heinze et al.

[11] Patent Number: 4,877,032

[45] Date of Patent: Oct. 31, 1989

[54] SENSOR ARRANGEMENT FOR THE CONTROL OF IMPLANTABLE DEVICES

[75] Inventors: Roland Heinze, Munich; Hans-Dieter Liess, Muensing, both of Fed. Rep. of Germany

[73] Assignees: Siemens Aktiengesellschaft, Berlin & Munich, Fed. Rep. of Germany; Siemens Aktiengesellschaft, Munich, Fed. Rep. of Germany

[21] Appl. No.: 333,805

[22] Filed: Apr. 6, 1989

Related U.S. Application Data

[63] Continuation of Ser. No. 51,856, May 20, 1987, abandoned.

[30] Foreign Application Priority Data

Jun. 16, 1986 [DE] Fed. Rep. of Germany ....... 3620277

[51] Int. Cl.$^4$ ............................................. A61N 1/00
[52] U.S. Cl. ......................... 128/419 PG; 128/419 R; 128/419 P; 128/695
[58] Field of Search ................ 128/419 PG, 634, 632, 128/635, 637, 642, 658, 673, 675, 692, 715, 716, 724, 768, 784, 786, 903

[56] References Cited

U.S. PATENT DOCUMENTS

| | | | |
|---|---|---|---|
| 3,638,640 | 2/1972 | Shaw | 128/633 |
| 3,800,801 | 4/1974 | Gaillard | 128/419 PT |
| 3,942,536 | 3/1976 | Mirowski et al. | 128/419 D |
| 4,266,554 | 5/1981 | Amagori | 128/633 |
| 4,374,382 | 2/1983 | Markowitz | 128/419 PT |
| 4,399,820 | 8/1983 | Wirtzfeld et al. | 128/419 PG |
| 4,407,288 | 10/1983 | Langer et al. | 128/419 PG |
| 4,543,955 | 10/1985 | Schroeppel | 128/635 |
| 4,549,548 | 10/1985 | Wittkampf et al. | 128/419 PG |
| 4,628,934 | 12/1986 | Pohndorf et al. | 128/419 PG |

FOREIGN PATENT DOCUMENTS 3152963  8/1984  Fed. Rep. of Germany.

OTHER PUBLICATIONS

"Integrated Signal Conditioning for Silicon Pressure Sensors", Borky et al., IEEE Transactions, Dec. 1979.
"Multi-Channel Personal Telemetry System Using PPM", Marki, Aerospace Medicine, vol. 32, 1961.
"A Multichannel Biotelemetry Transmitter Utilizing a PCM Subcarrier", Fryer et al., Biotelemetry II, 2nd Int. Symp., 1974.

Primary Examiner—Lee S. Cohen
Assistant Examiner—Kennedy J. Schaetzle
Attorney, Agent, or Firm—Hill, Van Santen, Steadman & Simpson

[57] ABSTRACT

A sensor arrangement for controlling an implantable device, such as a heart pacemaker, has a number of individual sensors connected to an evaluation circuit through a catheter having at least two leads. The sensors are respectively activated in chronological succession by a shared control circuit, with both the sensors and the control circuit being arranged in the catheter. The corresponding measured signals are transmitted via the same leads, and also being offset chronologically. The arrangement permits a number of sensors to be connected to a catheter while maintaining only two lines in the catheter, so that the flexibility and reliability of the catheter, which are best with the fewest possible leads, remain unimpaired.

18 Claims, 2 Drawing Sheets

SENSOR ARRANGEMENT FOR THE CONTROL OF IMPLANTABLE DEVICES

This is a continuation of application Ser. No. 051,856, filed May 20, 1987, now abandoned.

BACKGROUND OF THE INVENTION

1. Field of the Invention

The present invention relates to a sensor arrangement for controlling an implantable device, such as a heart pacemaker, and in particular to a sensor arrangement which is connected to an evaluation circuit via a catheter having at least two leads (bipolar catheter).

2. Description of the Prior Art

A sensor arrangement for a heart pacemaker is described in German OS No. 31 52 963. In this sensor arrangement, the blood oxygen saturation is acquired using a sensor disposed in a heart chamber, the sensor being connected to the heart pacemaker via a dual-pole catheter. In some instances, however, the acquisition of a plurality of measured parameters is desirable. In the case of heart pacemakers, for example, the blood oxygen saturation, the blood temperature, the blood pressure and the conductivity of the blood provide information about the frequency at which the heart pacemaker should stimulate the heart. Sensors for individually obtaining all of the above parameters cannot be accomodated in the heart pacemaker itself, so that the measured signals must be transmitted via the catheter. It is important that the catheter, however, contain the fewest possible number of leads for reasons of flexibility and reliability.

SUMMARY OF THE INVENTION

It is an object of the present invention to provide a sensor arrangement which permits a plurality of measured signals from a plurality of sensors to be transmitted using a catheter which requires the fewest possible number of leads.

The above object is achieved in accordance with the principles of the present invention in a sensor arrangement wherein a plurality of sensors are accomodated in a catheter, the sensors being activated in chronological succession by a common control circuit. The resulting measured signals are transmitted also in chronological succession via the electrical leads in the catheter.

As a result of the chronological offset (i.e., transmission and reception in succession) the various measured signals can be separated from each other without the necessity of a separate line in the catheter for each sensor.

The chronologically offset activation of the sensors can be achieved in a simple manner by connecting the sensors to the catheter leads via switches, and operating the switches in succession by a control circuit.

In one embodiment, the evaluation circuit controls activation of the sensors through the control circuit. Activation of the sensors is controlled by a decoder which receives coded trigger signals from the evaluation circuit via the leads of the catheter. The decoder decodes the coded trigger signals coming from the evaluation circuit, and directly drives the switches, or drives the switches through an additional function stage, for example, a counter.

The control circuit is preferably constructed such that it does not require a separate lead to the evaluation circuit, as this would require the use of a three-pole catheter. The control circuit is connected in parallel with the sensors across the two leads, without impairing the function of the sensors.

In another embodiment, the control circuit automatically controls activation of the sensors, whereby the resulting measured signals are provided with a coding associated with the driven sensor. The sensors can thereby be controlled in a simple manner by a timer circuit contained in the control circuit.

The coding may be undertaken on the basis of pulse phase modulation. This can be achieved by generating a zero mark in every measuring period by means of a signal lying outside of the range of measurement. Coding is achieved by measuring the distance of the coded signal from this zero mark.

Alternatively, coding can ensure using amplitude, pulse duration or pulse code modulation.

Each sensor in a further embodiment may have a shared signal transducer with a memory allocated thereto, whereby the memory stores the measured value from a sensor upon activation of the sensor, and the stored measured value is coded in a form suitable for the evaluation circuit. The coding is undertaken by the signal transducer following the measuring phase, and is then transmitted to the evaluation circuit. This embodiment is particularly suitable given sensors wherein the measured and transmitted signals are chronologically separated.

DESCRIPTION OF THE PREFERRED EMBODIMENTS

Figure 1:
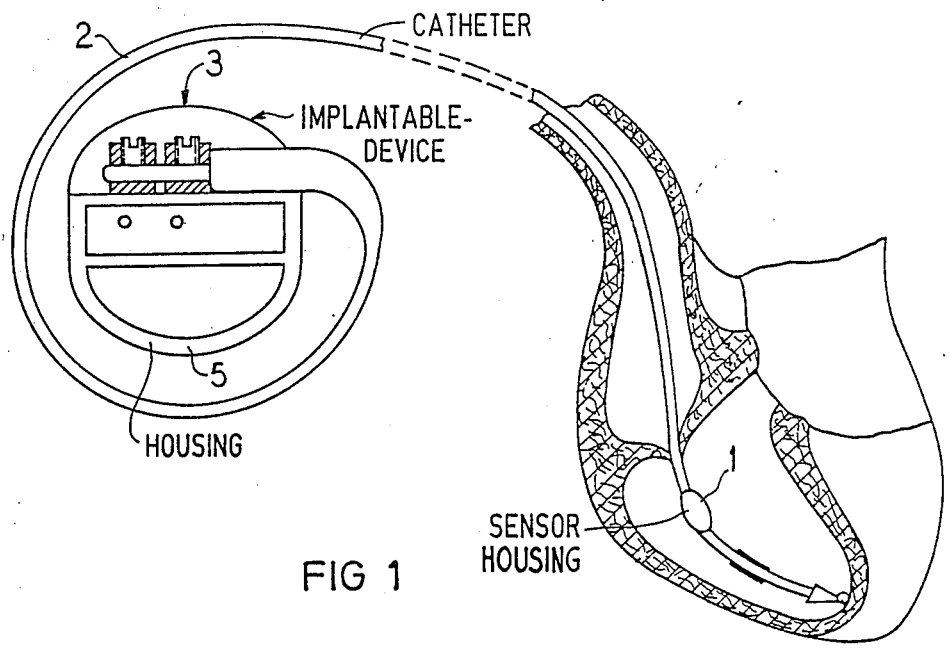
FIG. 1 schematically shows a sensor arrangement constructed in accordance with the principles of the present invention in relation to a human heart.

A sensor arrangement constructed in accordance with the principles of the present invention is shown in FIG. 1 for use in controlling an implantable device 3, having a housing 5. Components in a sensor housing 1 are connected via catheter 2 to an evaluation circuit 3a (shown in FIG. 2) in the implantable device 3. The catheter 2 has two leads 2a and 2b also shown in FIG. 2.

Figure 2:
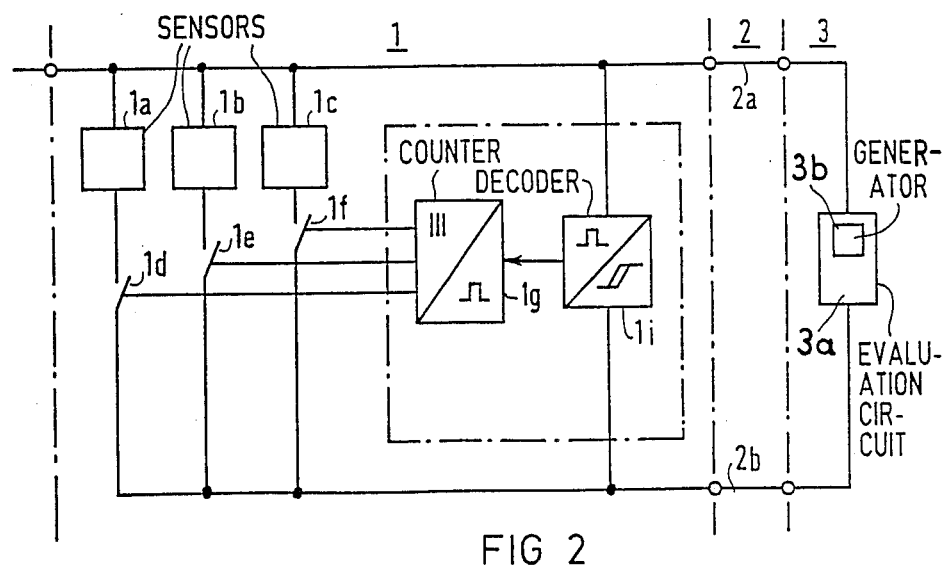
FIG. 2 is a block circuit diagram of a first embodiment of a sensor arrangement constructed in accordance with the principles of the present invention.

The sensor housing 1 has three sensors 1a, 1b and 1c in the exemplary embodiment, all of which are accomodated in the sensor housing coextensive with the vertical dot and dash lines in FIG. 2.

The individual sensors 1a, 1b and 1c are respectively connected to the lines 2a and 2b of the catheter 2 via switches 1d, 1e and 1f. The switches 1d, 1e and 1f are all operated by a counter 1g. The counter 1g may either be controlled by a clock generator 1h (see FIG. 3), contained in the housing 1 for the sensor, or by a decoder 1i through the evaluation circuit 3 and the lines 2a and 2b.

The lines 2a and 2b carry both the supply currents for the overall sensor stage contained within the housing 1, and the measuring currents. This is possible if the supply currents are negligibly small or constant in comparison to the measuring currents, so that the measuring currents can be acquired by subtracting the constant supply currents from the total current.

The switches 1d, 1e and 1f are respectively successively closed (switched to a conducting state) by the counter 1g in a chronologically offset manner. When one of the sensors, such as sensor 1a, for example, is activated, the sensor 1a determines the voltage or current at the leads 2a and 2b. On the basis of this voltage or current, or on the basis of a combination of a number of such voltage or current values, from a number of sensors, the evaluation circuit 3 can control a function of the implantable device 3, for example, the pulse rate of a heart pacemaker.

One of the sensors may, for example, be a sensor for the acquisition of blood oxygen saturation, as disclosed in the previously cited German OS No. 31 52 963.

Figure 3:
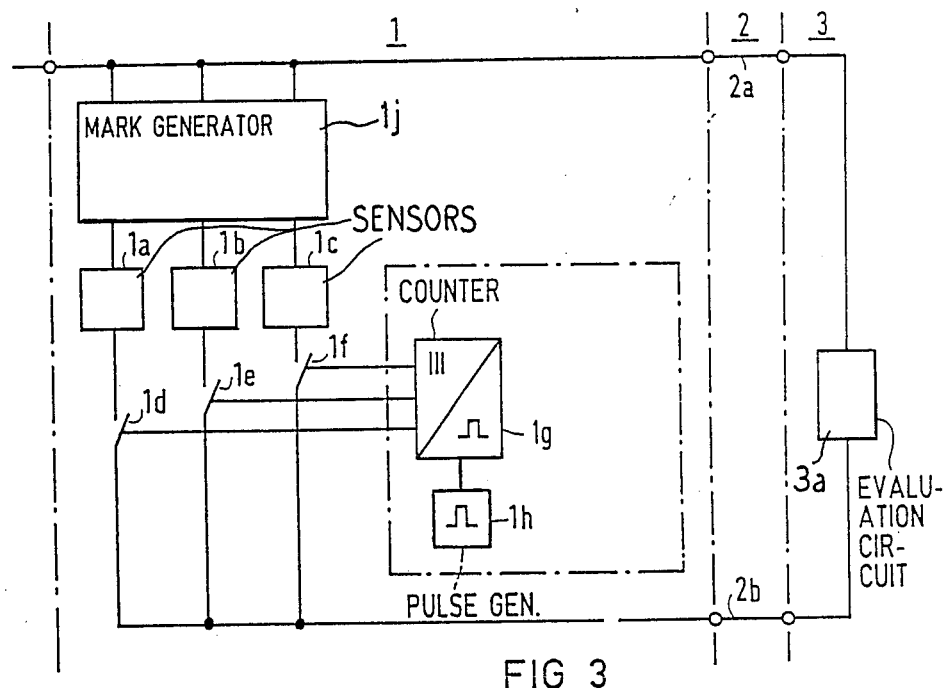
FIG. 3 is a block circuit diagram of a second embodiment of a sensor arrangement constructed in accordance with the principles of the present invention.

The counter 1g may, for example, be driven by an internal clock generator 1h arranged in the housing 1 for the sensor stage, the counter 1g and the clock generator 1h operating in combination as a timer circuit as shown in FIG. 3. In this case, the voltage or current signals must be provided with a coding associated with the driven sensor, so that the evaluation circuit 3a recognizes that sensor as the source of the incoming signal.

Alternatively, the evaluation circuit 3a may control the selection of the switches 1d, 1e and 1f, and thus activation of the sensors 1a, 1b and 1c. In this case, shown in FIGS. 2 and 4, a decoder 1i is driven by a generator 3b in the evaluation circuit 3a via the leads 2a and 2b. The decoder 1i controls the counter 1g in the exemplary embodiment. In this case, coded signals must be transmitted from the evaluation circuit 3a to the decoder 1i.

Pulse phase modulation is especially beneficial for coding the signals transmitted from the evaluation circuit 3a to the decoder 1i, or from the sensors 1a through 1c to the evaluation circuit 3a for identifying the signal source. In each measuring period, a zero mark is generated by a mark generator 1j from a signal lying outside of the range of measurement, as shown in FIG. 3. Using this zero mark, for example, the counter 1g can be reset to zero. Given a known clock period, a conclusion regarding which of the sensors 1a through 1c generated the incoming signal can be made based on the distance of the incoming (received) signal from the zero mark.

Figure 4:
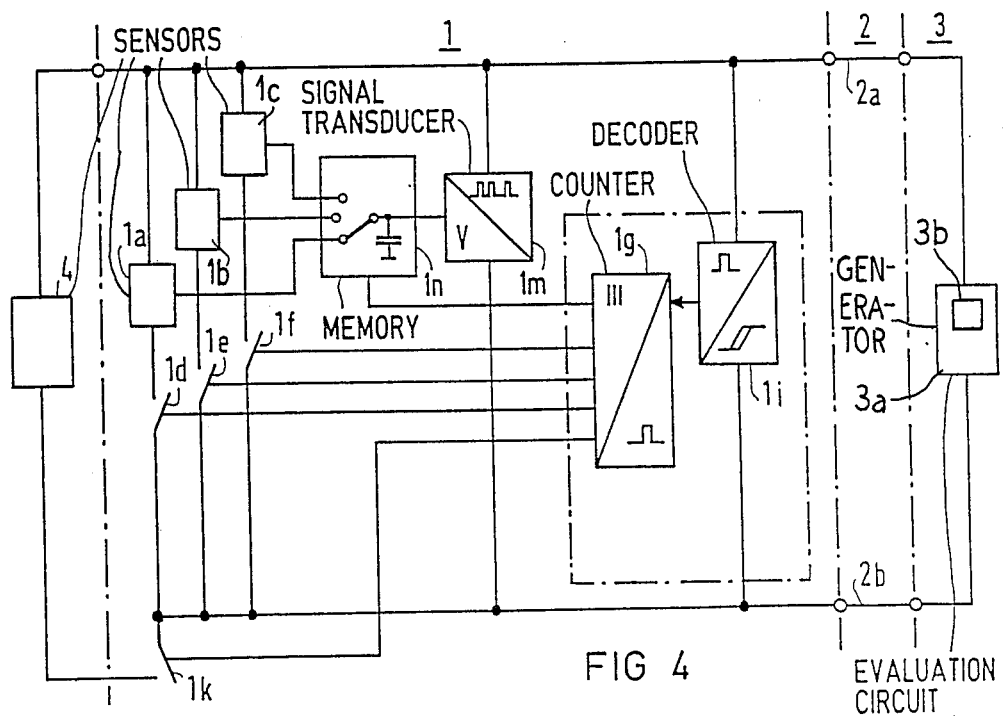
FIG. 4 is a block diagram of a third embodiment of a sensor arrangement having an additional sensor constructed in accordance with the principles of the present invention.

In a further embodiment shown in FIG. 4, the sensors 1a through 1c have a common memory 1n connectable to the sensors 1a through 1c. A signal transducer 1m is connected to the output of the memory 1n which may, for example, convert voltage into pulses. The signal transducer 1m is connected to the leads 2a and 2b. In this embodiment, the measured signal and the transmission signal are separated from each other, with the memory 1n storing the measured signal given activation of one of the sensors 1a through 1c. Chronologically following the measuring phase, the signal transducer 1m transmits the measured value to the evaluation circuit 3a in a coding adapted to the evaluation circuit 3a identifying the particular sensor.

The signal transducer 1m may use any standard modulation technique, such as amplitude, pulse phase, pulse duration or pulse code modulation.

In the embodiment of FIG. 4, an additional sensor 4 is disposed outside of the housing for the sensor stage 1, the additional sensor 4 being directly connected to the lead 2a, and being connected to the lead 2b via a switch 1k.

In a manner analogous to that of the internal sensors 1a through 1c, the switch 1k is controlled via the decoder 1i and the counter 1g. The sensor 4, for example, may be an EKG sensor or an impedance sensor, both of which are not capable of accomodation within the housing for the sensor stage 1.

Although modifications and changes may be suggested by those skilled in the art it is the intention of the inventors to embody within the patent warranted hereon all changes and modifications as reasonably and properly come within the scope of their contribution to the art.

We claim as our invention:

1. An apparatus for medically treating a patient comprising:

an implantable device which supplies a medical treatment to said patient, said device having at least one variable function;

a catheter connected to said device and also implantable in said patient, said catheter having a plurality of leads therein;

a plurality of sensors which respectively generate measured signals corresponding to different body parameters of said patient contained within said catheter;

control means in said catheter for successively respectively connecting said sensors across only two leads of said plurality of leads and thereby activating said sensors chronologically offset;

an evaluation means disposed in said implantable device remote from said sensors and connected to said sensors by said catheter for generating a signal for use in varying said variable function from said measured signals; and means for transmitting said respective measured signals from each activated sensor chronologically offset to said evaluation means via no more than said two leads.

2. An apparatus as claimed in claim 1, wherein said control means includes a plurality of switches respectively connected to said sensors, and means for operating said switches in a selected sequence.

3. An apparatus as claimed in claim 1, wherein said control means includes means responsive to signals from said evaluation means for activating said sensors.

4. An apparatus as claimed in claim 3, wherein said evaluation means includes means for generating coded trigger signals, and wherein said control means includes a decoder which receives said coded trigger signals via said leads and which causes activation of said sensors based thereon.

5. An apparatus as claimed in claim 1, wherein said control means includes means for coding said measured signals before transmission to said evaluation means so that the sensor which is the source for each measured signal can be identified by said evaluation circuit.

6. An apparatus as claimed in claim 5, wherein said means for coding includes a timer circuit.

7. An apparatus as claimed in claim 6, wherein said timer circuit consists of a counter connected to each of said sensors and a pulse generator connected to said counter.

8. An apparatus as claimed in claim 5, wherein said means for coding is a means for pulse phase modulation coding.

9. An apparatus as claimed in claim 8, wherein said means for coding includes means for generating a zero mark at a beginning of each measuring period, and wherein said means for pulse phase modulation is includes means measuring the distance of each coded trigger signal from the zero mark.

10. An apparatus as claimed in claim 1, further comprising means for encoding said measured signals using amplitude modulation.

11. An apparatus as claimed in claim 1, further comprising means for coding said measured signals using pulse duration modulation.

12. An apparatus as claimed in claim 1, further comprising means for coding said measured signals using pulse code modulation.

13. An apparatus as claimed in claim 1, further comprising a memory connected to each of said sensors and a signal transducer connected to an output of said memory, said memory storing each measured signal from a sensor upon activation of a sensor, and the stored measured value being converted by said signal transducer following completion of a measurement into a form for evaluation by said evaluation means.

14. An apparatus for medically treating a patient comprising:
 an implantable device which supplies a medical treatment to said patient, said device having at least one variable function;
 a catheter connected to said implantable device and also implantable in said patient, said catheter having a plurality of leads;
 a plurality of sensors contained within said catheter, each sensor generating a measured value signal upon activation thereof corresponding to a respective body parameter of said patient;
 a like plurality of switching means respectively connected to said sensors and also contained within said catheter for connecting said sensors across only two leads of said plurality of leads;
 an evaluation means disposed in said implantable device remote from said sensors and connected to said sensors by said catheter for generating a signal for use in varying said variable function from said measured value signals;
 a counter means connected to each of said switches for operating said switches to activate said sensors in a selected sequence in response to an input signal, each of said sensors, when activated, supplying its measured value signal via no more than said two leads to said evaluation means;
 and means for generating said input signal for said counter.

15. An apparatus as claimed in claim 14, wherein said means for generating said input signal is a pulse generator contained within said catheter and connected to said counter.

16. An apparatus as claimed in claim 14, wherein said evaluation means includes means for generating a coded trigger signal, and wherein said means for generating said input signal is a decoder connected across said leads within said catheter and having an output connected to said counter, said decoder decoding said coded trigger signal from said evaluation means and operating said counter based on the decoded signal.

17. An apparatus for medically treating a patient comprising:
 an implantable device which supplies a medical treatment to said patient, said device having at least one variable function;
 a catheter connected to said implantable device and also implantable in said patient, said catheter having a plurality of leads therein;
 a plurality of sensors contained within said catheter, each sensor generating an output signal upon activation thereof corresponding to a respective body parameter of said patient;
 a like plurality of switching means respectively connected to said sensors for connecting said sensors across only two leads of said plurality of leads;
 an evaluation means disposed in said implantable device remote from said sensors and connected to said sensors by said catheter for generating a signal for use in varying said variable function from said output signals of said sensors;
 a counter means connected to each of said switches for operating said switches to activate said sensors in a selected sequence based on a input signal to said counter each of said sensors when activated, supplying its output signal via no more than two leads to said evaluation means;
 means for generating said input signals; means connected to each of said sensors, to said counter and to said leads for encoding the output signals of said sensors for transmission to said evaluation means to identify the sensor producing the output signal.

18. An apparatus as claimed in claim 17, wherein said means for coding is a memory having means controlled by said counter for individually connecting said memory to said sensors in said selected sequence, and a signal transducer means connected to an output of said memory for converting the output of said memory into a signal for transmission to said evaluation means via said leads.

* * * * *